US008925196B2

(12) United States Patent
Ostein et al.

(10) Patent No.: US 8,925,196 B2
(45) Date of Patent: Jan. 6, 2015

(54) APPARATUS AND METHOD FOR REPLACING AN OIL PRESSURE REGULATING ASSEMBLY AND A HIGH PRESSURE RELIEF VALVE ASSEMBLY

(75) Inventors: Adam William Ostein, Edelstein, IL (US); Christopher Lee Bach, Chillicothe, IL (US); Patrick W. Savage, Jr., Washington, IL (US); Curtis John Graham, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 594 days.

(21) Appl. No.: 13/278,906

(22) Filed: Oct. 21, 2011

(65) Prior Publication Data

US 2013/0097832 A1    Apr. 25, 2013

(51) Int. Cl.
*B23P 6/00* (2006.01)
*F01M 1/16* (2006.01)
*F01L 1/46* (2006.01)
*F01M 1/10* (2006.01)

(52) U.S. Cl.
CPC .. *F01M 1/16* (2013.01); *B23P 6/00* (2013.01); *F01L 1/462* (2013.01); *F01M 2001/1085* (2013.01); *F01M 2001/1092* (2013.01)
USPC ................ 29/888.011; 29/896.91; 29/402.08; 267/226

(58) Field of Classification Search
CPC .............. B23P 6/00; F01L 1/462; B21F 3/02; F01M 1/16
USPC ........... 29/888.011, 888.42, 890.121, 896.91, 29/402.08, 225, 227; 267/226
See application file for complete search history.

(56) References Cited

U.S. PATENT DOCUMENTS

| 4,174,699 | A | 11/1979 | Gill |
| 2009/0199403 | A1 | 8/2009 | Younger |
| 2010/0192899 | A1 | 8/2010 | Ni et al. |

FOREIGN PATENT DOCUMENTS

| DE | 10345596 A1 | 4/2005 |
| EP | 0816645 A1 | 1/1998 |
| WO | 8302822 A1 | 8/1983 |

*Primary Examiner* — Jermie Cozart
(74) *Attorney, Agent, or Firm* — Miller, Matthias & Hull

(57) ABSTRACT

A method of increasing oil pressure in a heavy duty truck engine lubricating system is provided. The lubricating system comprises an oil pressure regulating assembly mounted in an oil filter base and having a main spring to regulate oil pressure, and a high pressure relief valve assembly mounted in the oil filter base and having a peak clipping spring to relieve oil pressure when the pressure exceeds a specified limit. The method includes the steps of replacing the main spring with a replacement main spring having a higher spring constant and replacing the peak clipping spring with a replacement peak clipping spring having a higher spring constant. A replacement kit for increasing oil pressure is also provided.

9 Claims, 7 Drawing Sheets

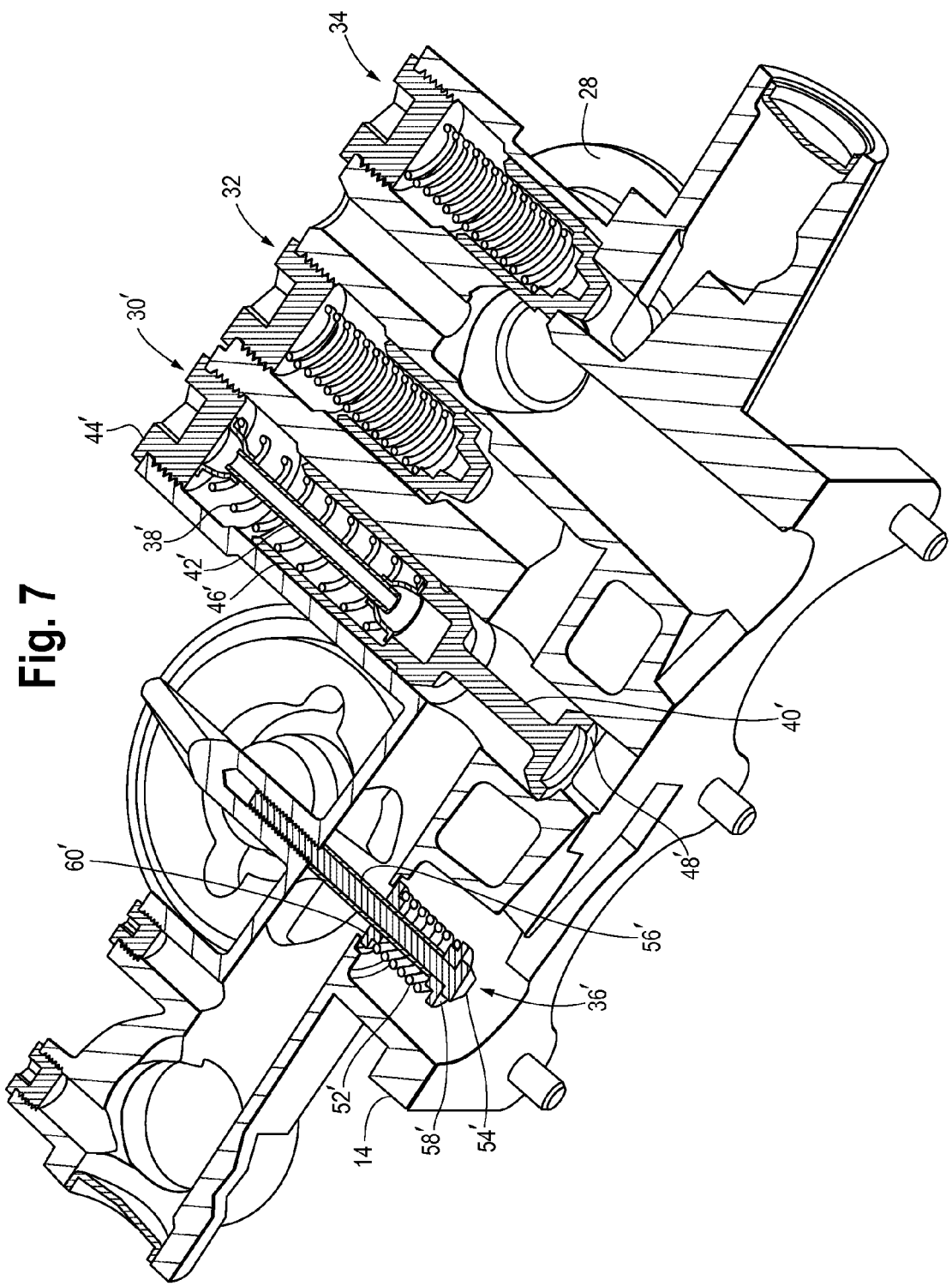

APPARATUS AND METHOD FOR REPLACING AN OIL PRESSURE REGULATING ASSEMBLY AND A HIGH PRESSURE RELIEF VALVE ASSEMBLY

TECHNICAL FIELD

This disclosure relates generally to lubricating systems for internal combustion engines. More particularly, this disclosure relates to an apparatus and method for replacing the oil pressure regulating assembly and high pressure relief assembly in a lubricating system used in heavy duty vehicles in order to increase oil pressure to within a specified range.

BACKGROUND

Internal combustion engines require lubricating systems to lubricate moving parts and to remove heat. In large internal combustion engines for use in heavy duty vehicles, an oil pump distributes oil throughout the engine and through an oil filter mounted on a filter base. The filter base may be equipped with an oil pressure regulating assembly and high pressure relief assembly.

Heavy duty engines such as truck engines can experience low oil pressure, especially near the end of the engine service life. This low pressure is the result of the lubricating system lacking the capacity to absorb increased oil flow demands created by normal engine wear over the life of the engine. Replacing the engine block and/or crankshaft can bring the oil pressure up past the minimum specification, but is very expensive.

SUMMARY OF THE DISCLOSURE

A less expensive solution to the problem of low oil pressure has been developed in which a kit is provided to replace the original oil pressure regulator spring ("main spring") with a new main spring and to replace the original high pressure relief spring ("peak clipping spring") with a new peak clipping spring. The new main spring is stiffer than the original main spring to increase oil pressure without over-pressuring the filter or lubricating system. The new main spring may be made from a different material to minimize or limit variability in oil pressure.

In accordance with one aspect of the present disclosure, there is provided a method of increasing oil pressure in a heavy duty truck engine lubricating system. The lubricating system comprises an oil pressure regulating assembly mounted in an oil filter base and having a main spring to regulate oil pressure, and a high pressure relief valve assembly mounted in the oil filter base and having a peak clipping spring to relieve oil pressure when the pressure exceeds a specified limit. The method includes the steps of replacing the main spring with a replacement main spring having a higher spring constant and replacing the peak clipping spring with a replacement peak clipping spring having a higher spring constant.

The method may comprise the further steps of providing a replacement regulator valve and mounting it within the oil filter base housing; providing a replacement flared tube for holding the replacement main spring in a pre-compressed state; installing the replacement flared tube and replacement main spring within the housing so that one end of the replacement flared tube abuts the replacement regulator valve; and providing a replacement plug having a partially threaded cylindrical body for threadably connecting the replacement plug to the oil filter base so that it abuts an end of the flared tube, then torqueing the replacement plug to a specified torque.

The method may comprise the still further steps of providing a replacement tube and mounting it within the oil filter base, the replacement tube having a hollow interior for receiving a replacement bolt; providing a replacement second washer and slidably mounting it over the replacement tube so that it abuts the oil filter base; providing a replacement bolt having a partially threaded cylindrical body and a head; providing a replacement first washer slidably mounted over the bolt body so that it abuts the head; sliding the replacement peak clipping spring over the replacement bolt and installing the replacement bolt inside the replacement tube so that the replacement peak clipping spring is slightly compressed between the two replacement washers and biases the replacement second washer against the housing; and torqueing the replacement bolt to a specified torque.

BRIEF DESCRIPTION OF THE DRAWINGS

FIG. 7 is a sectional view of the oil filter base of FIG. 6 showing the replacement pressure regulating spring assembly and a replacement high pressure relief valve assembly after installation.

DETAILED DESCRIPTION

While this invention may be embodied in many forms, there is shown in the figures and will herein be described in detail one or more embodiments, with the understanding that this disclosure is to be considered an exemplification of the principles of the invention and is not intended to limit the invention to the illustrated embodiments.

Figure 1:
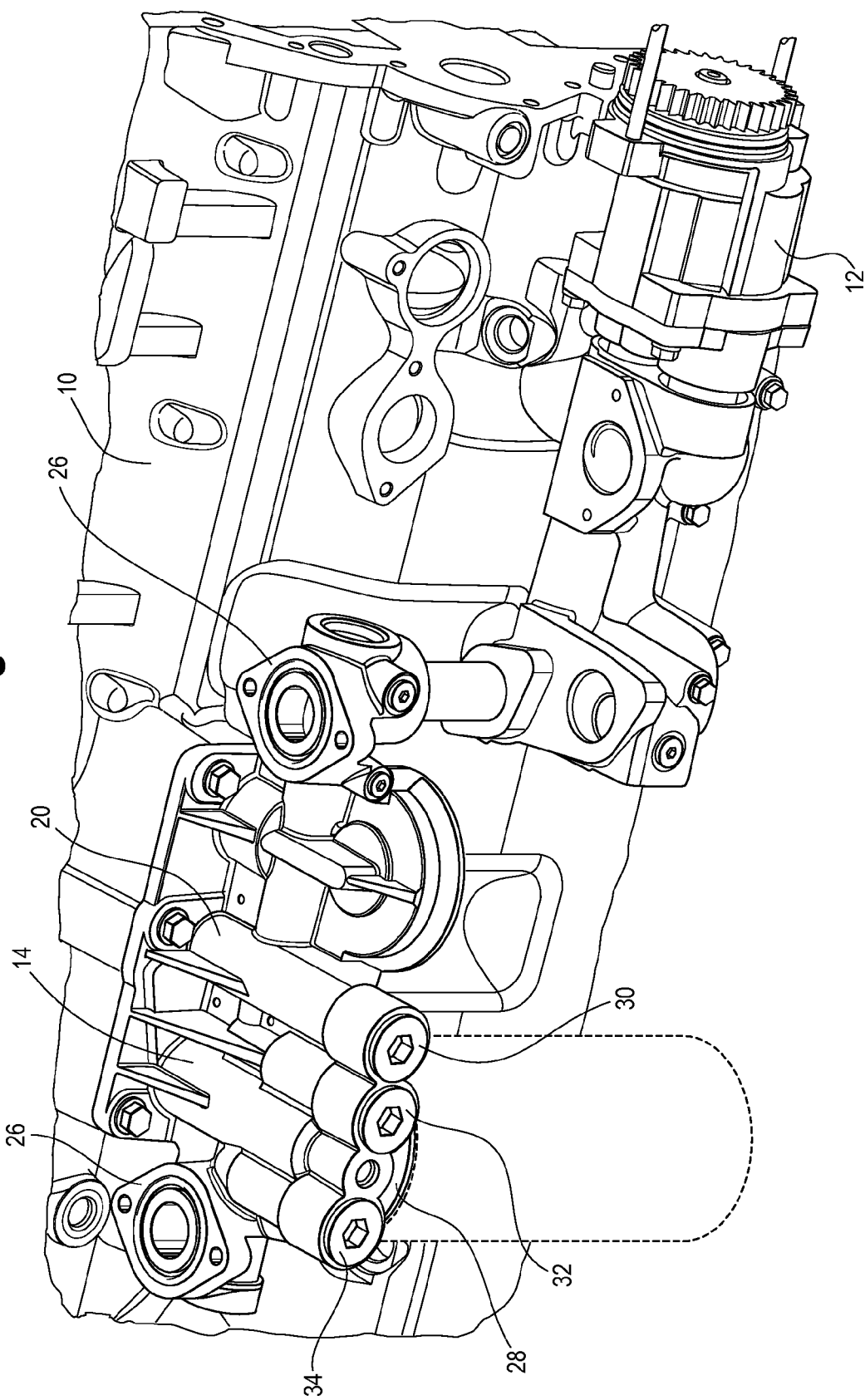
FIG. 1 is a partial perspective view of an engine block and lubricating system, including an oil pump, oil filter base and oil filter.

FIG. 1 shows a lubricating system mounted to an engine block 10, comprising an oil pump 12, oil filter base 14 and oil filter (shown in phantom lines). The oil pump 12 forces oil from the engine block 10 into the oil filter base 14 and up through an oil cooler (not shown) mounted on the oil filter base 14. After cooling, the oil re-enters the oil filter base 14 and passes through the oil filter before re-entering the oil filter base 14 once more on its way back to the engine block 10.

Figure 2:
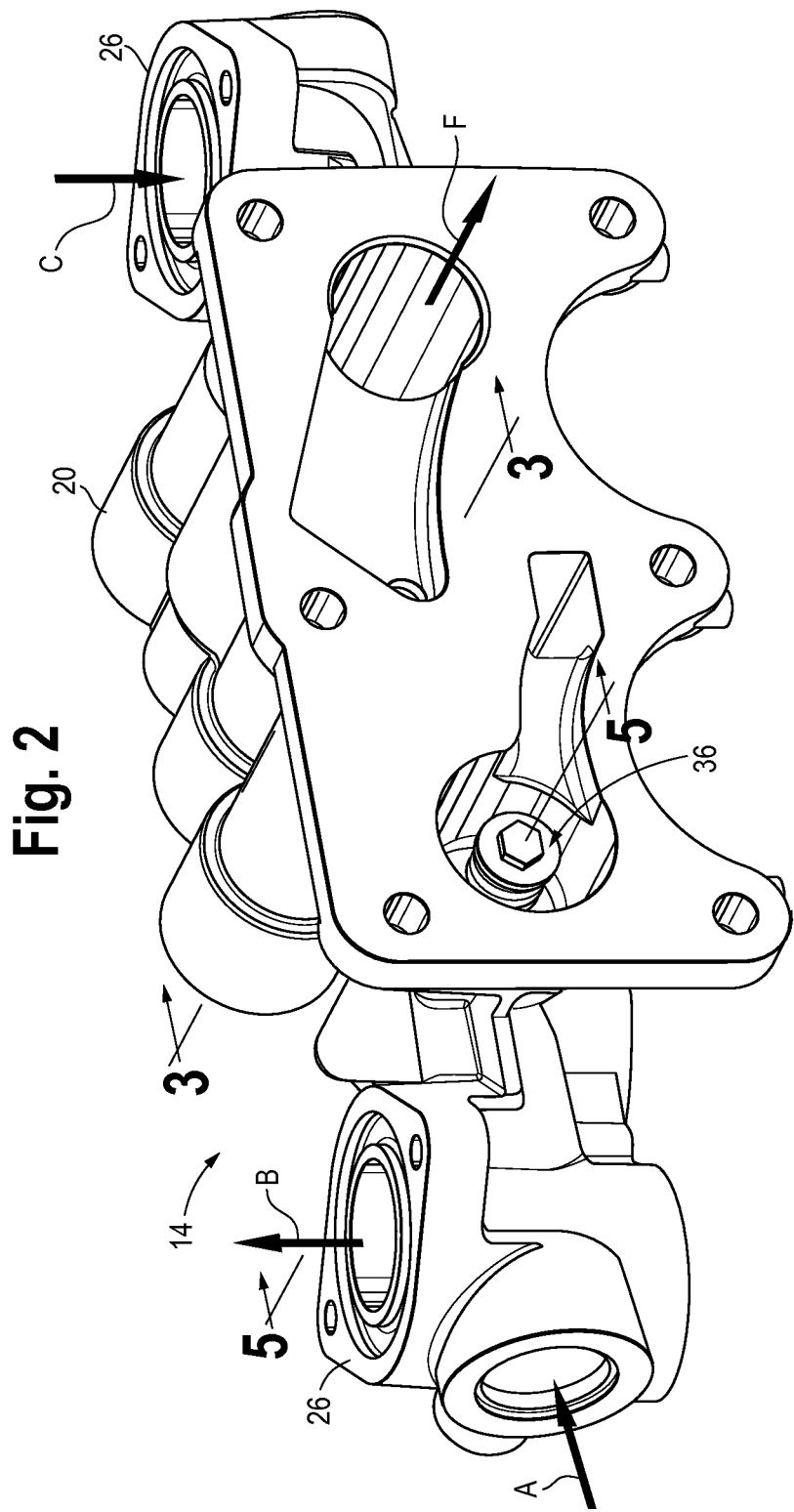
FIG. 2 is a rear perspective view of the oil filter base of FIG. 1 shown from the engine block side to reveal the high pressure relief valve assembly.
Figure 4:
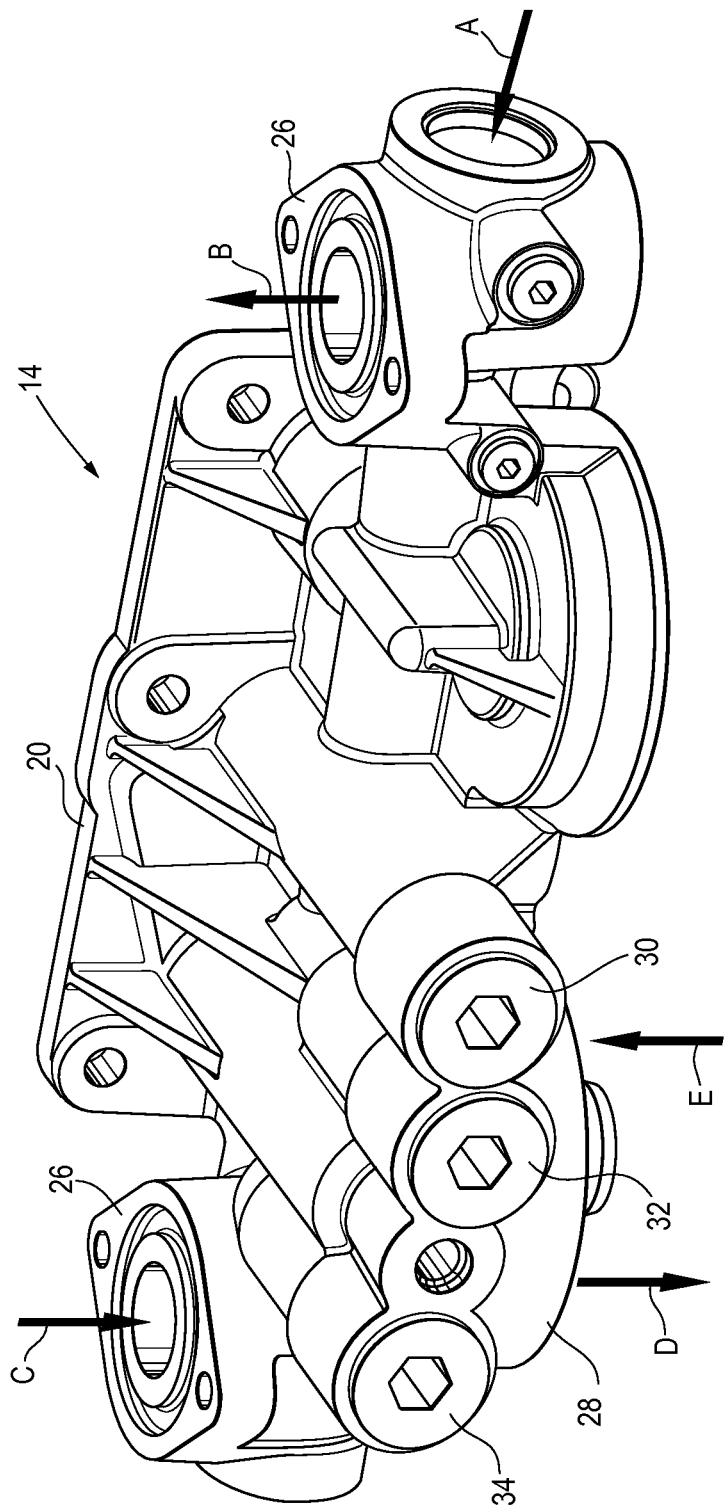
FIG. 4 is a front perspective view of the oil filter base of FIG. 1.

Referring to FIGS. 2 and 4, the oil paths through the oil filter base 14 will now be explained in detail. Oil from the oil pump 12 enters the oil filter base 14 through a first port as shown by arrow A and enters the oil cooler as shown by arrow B. Oil from the oil cooler reenters the oil filter base 14 as shown by arrow C and then to the oil filter as shown by arrow D. Filtered oil enters the oil filter base 14 as shown in arrow E on its return to the engine block 10 as shown in arrow F.

Referring to FIGS. 1 and 2, the oil filter base 14 comprises a housing 20, oil cooler mounting plates 26, a downwardly facing oil filter mounting plate 28, a pressure regulating spring assembly 30, a cooler bypass valve assembly 32, an engine filter bypass assembly 34, and a high pressure relief valve assembly 36.

Figure 3:
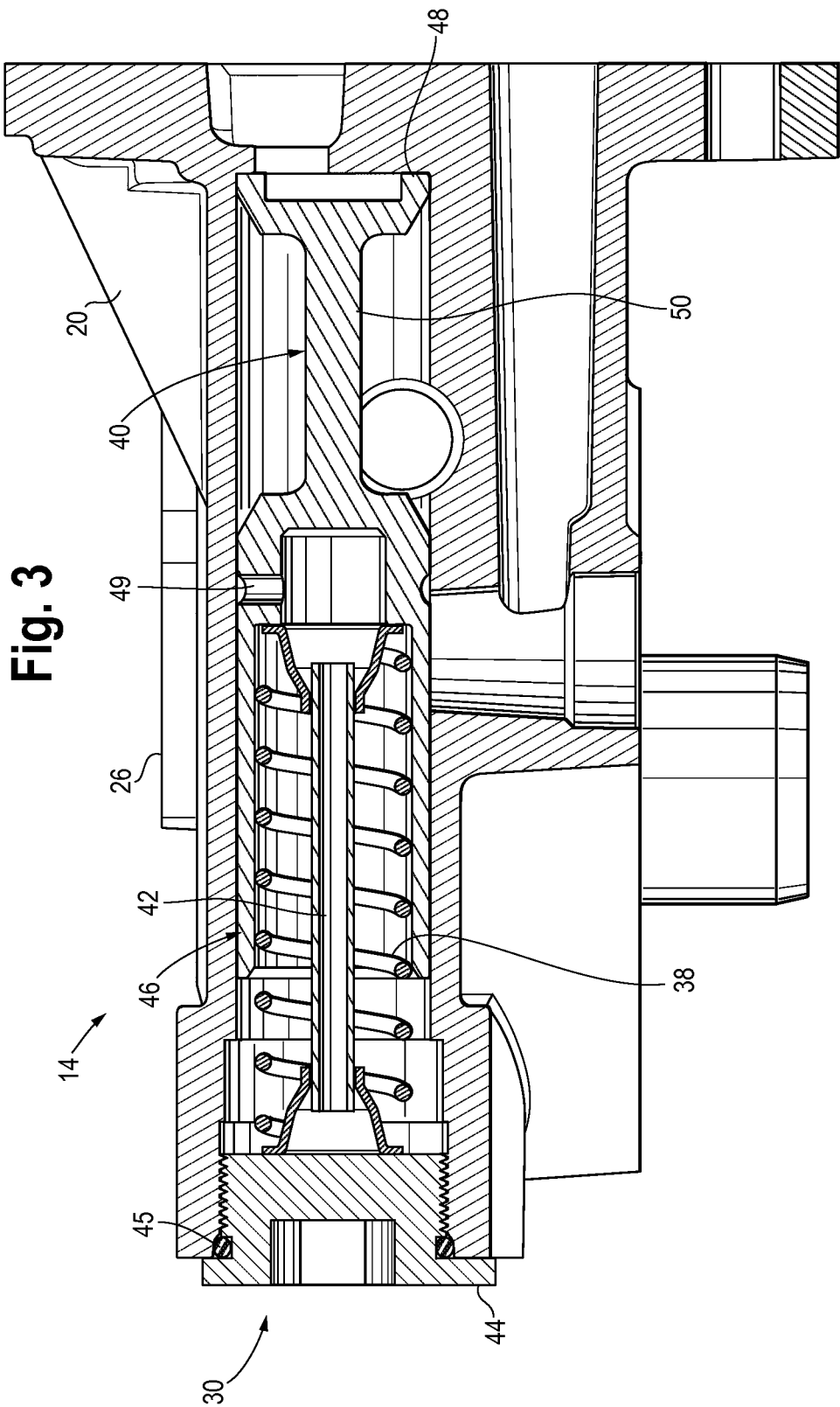
FIG. 3 is a cross sectional view of the oil filter base of FIG. 2 taken along line 3-3, showing the pressure regulating spring assembly.

As best shown in FIG. 3, the pressure regulating spring assembly 30 comprises a main spring 38, a regulator valve 40, a flared tube 42 and a plug 44. The main spring 38 typically is made from music wire, a high-carbon steel alloy, with a typical wire diameter of 2.49 mm. In one particular engine the main spring 38 had 18.05 coils, a solid (compressed) height of 45.426 mm and a free (uncompressed) height of 124.71 mm. The distal end of the main spring 38 (nearest the engine block) impinges on (presses against) on the regulator valve 40 and the proximal end presses against the plug 44.

The regulator valve 40 comprises a substantially cylindrical, hollow spring housing 46 connected to a valve seat 48 by a stem 50. The main spring 38 fits partially within and presses against the housing 46 near the stem 50, thereby biasing the valve seat 48 against the filter base housing 20. An O-ring (not shown) fits within a circumferential groove 49 formed in the outer surface of the regulator valve 40 and contacts the cylindrical oil filter housing wall to provide a sliding seal.

The flared tube 42 comprises a center tube and flared, bell shaped ends and serves to hold the main spring 38 in a pre-compressed state to aid in assembly. The flared, bell shaped ends are slidably connected to the center tube to allow compression and expansion of the main spring 38 during engine operation in response to oil pressure. When installed, the proximal end of the flared tube 42 (farthest from the engine block 10) abuts the plug 44 and the distal end of the flared tube 42 abuts the regulator valve 40.

The plug 44 has a cylindrical body that is partially threaded. An O-ring 45 is fitted around the body outer diameter to provide an oil tight seal with the oil filter base housing 20.

During engine operation, the regulator valve 40 moves in response to changing oil pressure to regulate the oil pressure, compressing and expanding the main spring 38. As the valve seat 48 opens, oil is diverted from the engine block 10 through a passage in the oil filter base 14 where it mixes with oil from the oil pump 12 before entering the oil cooler (not shown). Typically the valve seat 48 is closed during idling, opens when the engine speed reaches about 1000 RPM, and then travels back and forth during operation to regulate oil pressure.

Figure 5:
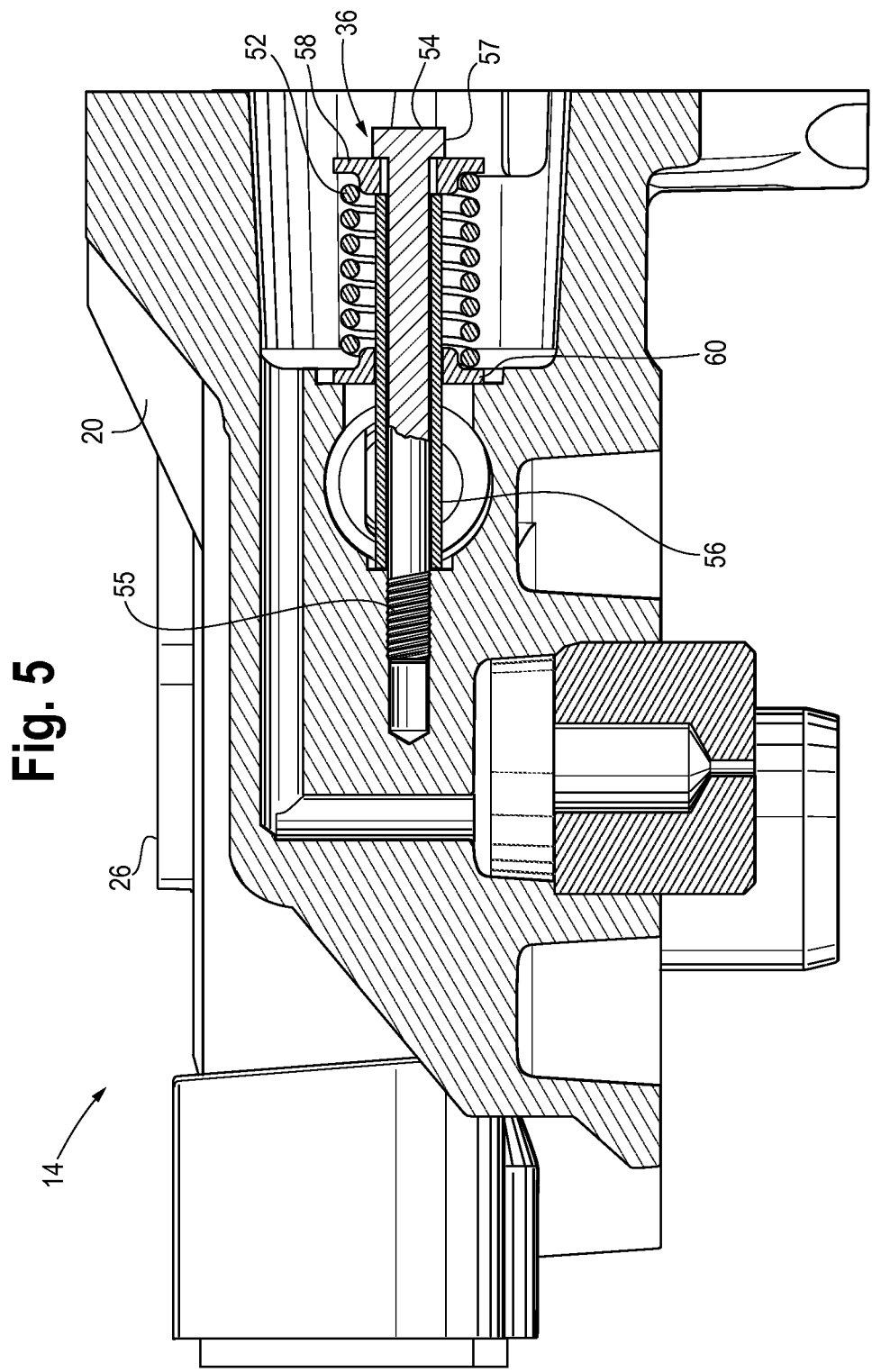
FIG. 5 is a cross sectional view of the oil filter base of FIG. 2 taken along line 5-5, showing the high pressure relief valve assembly.

As shown in FIG. 5, the high pressure relief valve assembly 36 comprises a peak clipping spring 52, a bolt 54, a tube 56, a first washer 58 and a second washer 60. The bolt 54 comprises a cylindrical body having a threaded (distal) end 55 and a head 57. The hollow cylindrical tube 56 is receivable within the oil filter base 14 on the side of the oil filter base 14 facing the engine block 10 and is configured to receive the second washer 60. The peak clipping spring 52 and first washer 58 can be slidably received over the tube 56 or bolt body with the first washer 58 abutting the bolt head 57. The bolt 54 can be inserted into the hollow tube 56 and threadably connected to the oil filter base 14. With the bolt 54 secured to the oil filter base 14 the peak clipping spring 52 is slightly compressed between the two washers 58, 60.

The peak clipping spring 52 biases the second washer 60 (which functions as a valve seat) against the filter base housing 20. During engine operation the second washer 60 is usually in this closed position. Oil passing though the oil filter base 14 exerts pressure on the side of the second washer 60 away from the peak clipping spring 52. If the engine oil pressure exceeds a set limit, the oil forces open the second washer 60, compressing the peak clipping spring 52 and creating an annular opening through which oil can be diverted from the engine lubricating system into the oil pan. This high oil pressure phenomenon can occur in very cold conditions when the oil is cold and relatively thick.

Heavy duty truck engines and off road vehicle engines can experience low oil pressure near the end of the engine service life. This low pressure is the result of the lubricating system lacking the capacity to absorb increased oil flow demands created by normal engine wear over the life of the engine. In accordance with one aspect of the invention, there is provided a kit for replacing the oil pressure regulator main spring 38 with a replacement main spring 38', and for replacing the peak clipping spring 52 with a replacement peak clipping spring 52'.

Figure 6:
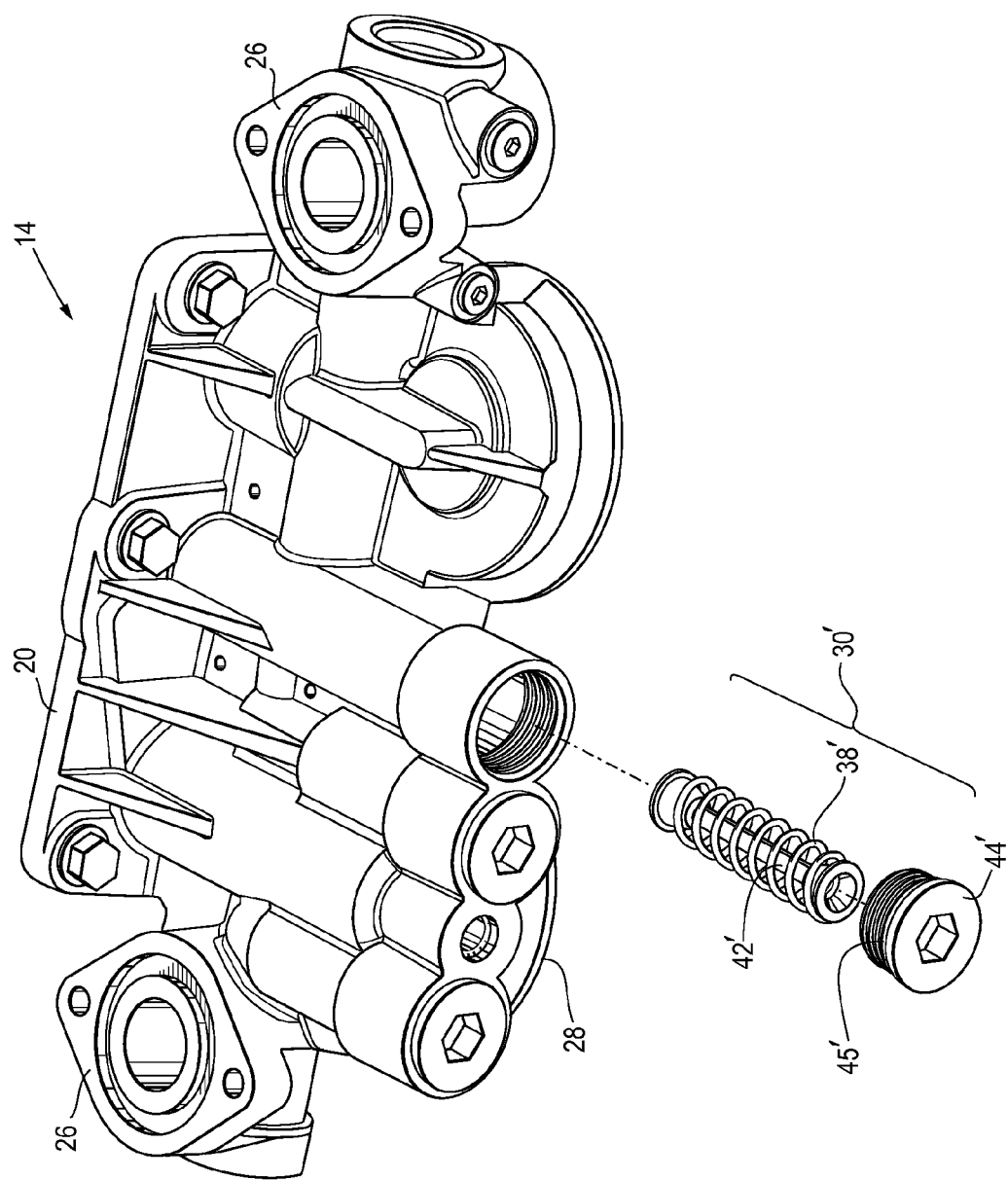
FIG. 6 is a perspective view of a replacement pressure regulating spring assembly being installed into an oil filter base.

The kit may comprise a replacement pressure regulating spring assembly 30' and a replacement high pressure relief valve assembly 36'. As shown in FIGS. 6 and 7, the replacement pressure regulating spring assembly 30' may comprise the replacement main spring 38', a replacement regulator valve 40', a replacement flared tube 42', a replacement plug 44' and a replacement O-ring 45'. In an exemplary embodiment the replacement main spring 38' is about ten percent stiffer (and so has a higher spring constant) than the original (replaced) main spring 38 and may be made from a different material (such as chrome silicon spring steel) to resist fatigue and limit oil pressure variability during operation. The replacement main spring 38' should be designed so that it does not overpressure the oil filter or the lubricating system.

The following Table A is a comparison of specifications for an exemplary original main spring 38 to an exemplary replacement main spring 38'. As indicated by the higher load at the same spring compression (96.2 mm), the replacement main spring 38' is stiffer than the original main spring 38.

TABLE A

| Material | Original Main Spring Music Wire | Replacement Main Spring Chrome Silicon |
| --- | --- | --- |
| Wire diameter, mm | 2.49 | 2.49 |
| Total Coils | 18.05 | 16.58 |
| Load at 96.52 mm (N) | 92.19 | 109.5 |

Replacement of the peak clipping spring 52 in addition to the main spring 38, and in some cases replacing both assemblies 30, 36, may be necessary, because if the peak clipping spring 52 isn't sufficiently stiff it will bleed off oil into the oil pan, thereby reducing the pressure gain accomplished by replacing the main spring 38.

FIG. 7 shows both replacement spring assemblies 30', 36' after installation. The replacement high pressure relief valve assembly 36' may comprise a replacement peak clipping spring 52', a replacement bolt 54', a replacement tube 56', a replacement first washer 58' and a replacement second washer 60'. Like the replacement main spring 38', the replacement peak clipping spring 52' has a higher spring constant (i.e., is stiffer) than the original peak clipping spring 52.

In another aspect of the invention there is provided a method of replacing an main (oil pressure regulator) spring 38 with a replacement main spring 38', and for replacing a peak clipping spring 52 (for high pressure relief) with a replacement peak clipping spring 52'. An exemplary method comprises the following steps:

I. Pressure Regulating Spring Assembly 30 Replacement:

Step 1: Slowly removing the pressure regulating spring assembly 30 from the oil filter base by removing the plug 44 and pulling out the rest of the assembly 30.

Step 2: Placing the replacement O-ring 45' on the replacement plug 44'.

Step 3: Installing the replacement spring assembly 30' in the oil filter base 14.

Step 4: Torqueing the replacement plug 44' to the specified torque.

II. High Pressure Relief Valve Assembly 36 Replacement:

Step 1: Removing bolt 54 using a socket wrench and removing the rest of the high pressure relief valve assembly 36.

Step 2: Installing the replacement high pressure relief valve assembly 36' in the oil filter base 14.

Step 3: Installing the replacement bolt 54'.

Step 4: Torqueing the replacement bolt 54' to the specified torque, preferably 12+/−3 Newton-meters.

EXAMPLE

Table B shows the increase in oil pressure achieved after replacing the old (original) main spring 38 and peak clipping spring 52 with a replacement main spring 38' and a replacement peak clipping spring 52'. When the engine is operating, either before or after replacement of the springs 38, 52, the oil pressure tends to rise rapidly until about 1300 RPM before leveling off. Replacing the springs 38, 52 resulted in an increase in oil pressure throughout almost the entire range of engine speeds, with the largest increases (of over 10%) occurring in the range of about 900-1800 RPM. For example, at 900 RPM (low idle) the oil pressure was raised to 24 psi from 19 psi.

TABLE B

| Engine Speed (RPM) | Oil Pressure With Replacement Springs (psi) | Oil Pressure With Old Springs (psi) | % Increase in Oil Pressure |
| --- | --- | --- | --- |
| 700 | 16 | 18 | −12.50 |
| 800 | 20 | 18 | 10.00 |
| 900 | 24 | 19 | 20.83 |
| 1000 | 28 | 22 | 21.43 |
| 1300 | 36 | 30 | 16.67 |
| 1500 | 37 | 32 | 13.51 |
| 1700 | 39 | 35 | 10.26 |
| 1800 | 40 | 36 | 10.00 |
| 2000 | 41 | 39 | 4.88 |

It is understood that the embodiments of the invention described above are only particular examples which serve to illustrate the principles of the invention. Modifications and alternative embodiments of the invention are contemplated which do not depart from the scope of the invention as defined by the foregoing teachings and appended claims. It is intended that the claims cover all such modifications and alternative embodiments that fall within their scope.

The invention claimed is:

1. A kit for replacing a main spring and a peak clipping spring in an oil filter base, the oil filter base including a housing mountable to a truck engine block for forming part of the engine lubricating system, an oil pressure regulating assembly mounted in the oil filter base housing, the oil pressure regulating assembly including, a stem, a spring housing disposed at a first end of the stem, a valve seat disposed at a second end of the stem opposite to the first end, and the main spring disposed inside the spring housing and configured to bias the valve seat disposed in a first position against the filter base housing, the main spring made of a material and having a spring constant, and the peak clipping spring having a spring constant and being a component of a high pressure relief valve assembly mounted in the housing for relieving oil pressure when the oil pressure exceeds a pre-determined limit when operably connected to the engine lubricating system, the kit comprising:

a replacement main spring having a higher spring constant than the spring constant of the main spring and made from a material more resistant to fatigue than the main spring material, the replacement main spring having a height configured to bias the valve seat disposed in the first position against the filter base housing.

2. The kit of claim 1 wherein the replacement main spring is made from chrome silicon steel alloy.

3. The kit of claim 1 further comprising:

a replacement peak clipping spring having a higher spring constant than the spring constant of the peak clipping spring.

4. The kit of claim 1 further comprising:

a replacement spring housing mountable within filter base housing;

a replacement plug having a partially threaded cylindrical body for threadably connecting the replacement plug to the oil filter base; and a replacement flared rod for holding the replacement main spring in a pre-compressed state and having opposing ends configured to abut the replacement spring housing and the replacement plug respectively when installed.

5. The kit of claim 4 further comprising:

a replacement bolt having a partially threaded cylindrical body and a head, the replacement bolt being threadably mountable to the oil filter base;

a replacement tube receivable within the oil filter base and having a hollow interior for receiving the replacement bolt;

a replacement first washer slidably mountable over the bolt body so that it abuts the head; and a replacement second washer slidably mountable over the replacement tube so that it abuts the oil filter base to form a seal therewith;

wherein the replacement peak clipping spring can be slidably received over the replacement tube so that it is slightly compressed between the two replacement washers and biases the replacement second washer against the housing.

6. A method of increasing oil pressure in a heavy duty truck engine lubricating system comprising an oil pressure regulating assembly mounted in an oil filter base housing, the oil pressure regulating assembly including a main spring to regulate oil pressure, a stem, a spring housing at a first end of the stem and a valve seat disposed at a second end of the stem opposite to the first end, the main spring disposed inside the spring housing and configured to bias the valve seat disposed in a first position against the filter base housing, a high pressure relief valve assembly mounted in the oil filter base and having a peak clipping spring to relieve oil pressure when it exceeds a specified limit, the main spring having a spring constant, the peak clipping spring having a spring constant, the method comprising the steps of:

replacing the main spring with a replacement main spring having a higher spring constant than the spring constant of the main spring, replacement main spring having a height configured to bias the valve seat disposed in the first position against the filter base housing; and biasing the valve seat disposed in the first position against the filter base housing with the replacement main spring, wherein the first position of the valve seat in the oil filter base housing when the valve seat is biased by the replacement main spring is the same as the first position of the valve seat when the valve seat is biased by the main spring.

7. The method of claim 6 further comprising the step of:
replacing the peak clipping spring with a replacement peak clipping spring having a higher spring constant than the spring constant of the peak clipping spring.

8. The method of claim 7 comprising the further steps of:
providing a replacement spring housing and mounting the replacement spring housing within filter base housing;

providing a replacement flared tube for holding the replacement main spring in a pre-compressed state;

installing the replacement flared tube and replacement main spring within filter base housing so that one end of the replacement flared tube abuts the replacement spring housing; and providing a replacement plug having a partially threaded cylindrical body for threadably connecting the replacement plug to the oil filter base so that it abuts an end of the flared tube, then torqueing the replacement plug to a specified torque.

9. The method of claim 8 further comprising the steps of:
providing a replacement tube and mounting it within the oil filter base, the replacement tube having a hollow interior for receiving a replacement bolt;

providing a replacement second washer and slidably mounting it over the replacement tube so that it abuts the oil filter base;

providing a replacement bolt having a partially threaded cylindrical body and a head;

providing a replacement first washer slidably mounted over the bolt body so that it abuts the head;

sliding the replacement peak clipping spring over the replacement bolt and installing the replacement bolt inside the replacement tube so that the replacement peak clipping spring is slightly compressed between the two replacement washers and biases the replacement second washer against the housing; and torqueing the replacement bolt to a specified torque.

\* \* \* \* \*

UNITED STATES PATENT AND TRADEMARK OFFICE
CERTIFICATE OF CORRECTION

| | | |
|---|---|---|
| PATENT NO. | : 8,925,196 B2 | Page 1 of 1 |
| APPLICATION NO. | : 13/278906 | |
| DATED | : January 6, 2015 | |
| INVENTOR(S) | : Ostein et al. | |

It is certified that error appears in the above-identified patent and that said Letters Patent is hereby corrected as shown below:

In the claims

Column 6, line 67, Claim 6, delete "replacement" and insert -- the replacement --.

Signed and Sealed this
Twenty-fourth Day of November, 2015

Michelle K. Lee
*Director of the United States Patent and Trademark Office*